United States Patent [19]

Werner

[11] Patent Number: 5,423,843
[45] Date of Patent: Jun. 13, 1995

[54] RETRACTABLE SURGICAL KNIFE

[76] Inventor: Richard S. Werner, 2920 W. 38th St., Minneapolis, Minn. 55410

[21] Appl. No.: 161,662

[22] Filed: Dec. 3, 1993

Related U.S. Application Data

[63] Continuation-in-part of Ser. No. 986,139, Dec. 4, 1992, Pat. No. 5,292,329.

[51] Int. Cl.$^6$ .............................................. A61B 17/32
[52] U.S. Cl. .................................... 606/167; 606/170; 401/113; 30/162
[58] Field of Search ................ 606/167, 170, 171, 172, 606/181, 182; 401/109, 112, 113, 114; 30/162, 164

[56] References Cited

U.S. PATENT DOCUMENTS

| | | | |
|---|---|---|---|
| 2,446,044 | 7/1948 | Davis | 401/103 |
| 2,905,146 | 9/1959 | Johmann | 401/103 |
| 3,144,005 | 8/1964 | Johmann | 401/103 |
| 3,657,812 | 4/1972 | Lee . | |
| 3,906,626 | 9/1975 | Riuli | 30/320 |
| 5,071,426 | 12/1991 | Dolgin et al. . | |
| 5,116,351 | 5/1992 | Frassetti . | |
| 5,139,507 | 8/1992 | Dolgin et al. . | |
| 5,141,517 | 8/1992 | Shutt . | |
| 5,250,063 | 10/1993 | Abidin et al. | 606/167 |
| 5,292,329 | 3/1994 | Werner | 606/167 |
| 5,306,237 | 4/1994 | Clement et al. | 604/30 |

*Primary Examiner*—C. Fred Rosenbaum
*Assistant Examiner*—Bryan Leander Tsosie
*Attorney, Agent, or Firm*—Merchant, Gould, Smith, Edell, Welter & Schmidt

[57] ABSTRACT

A retractable "ball-pen" like tool/scalpel, provided with a latch mechanism, is automatically retracted when not in use by pushing the latch mechanism and is extended when in use by pushing a tool/blade support member of the tool/scalpel. The latch mechanism is engaged with the tool/blade support member when the tool/blade support member is pushed to an operative position wherein a tool/blade is exposed from a sheath member. The latch mechanism is pushed transversely and disengaged with the tool/blade support member whereby the tool/scalpel is retracted into the sheath member.

17 Claims, 9 Drawing Sheets

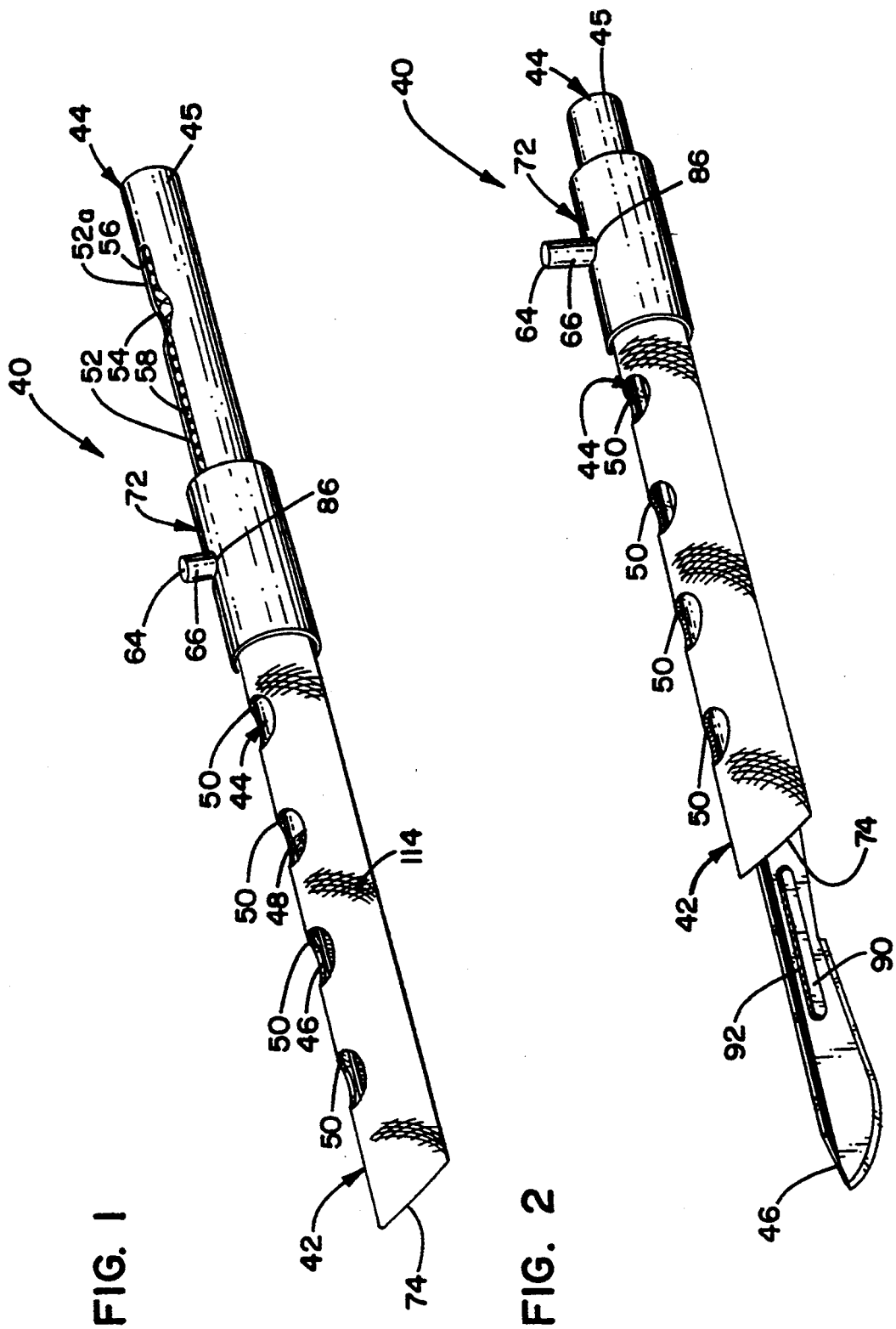

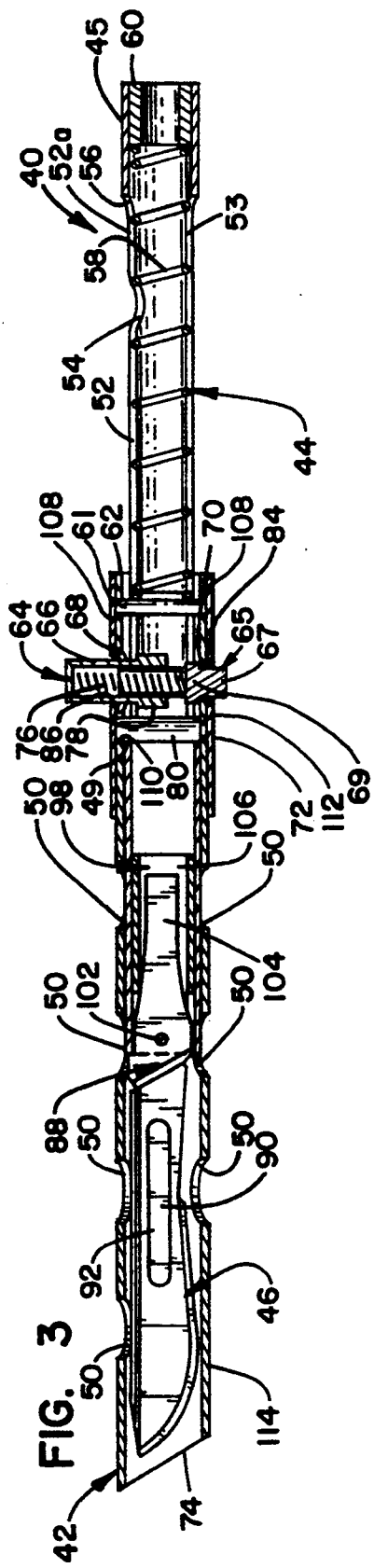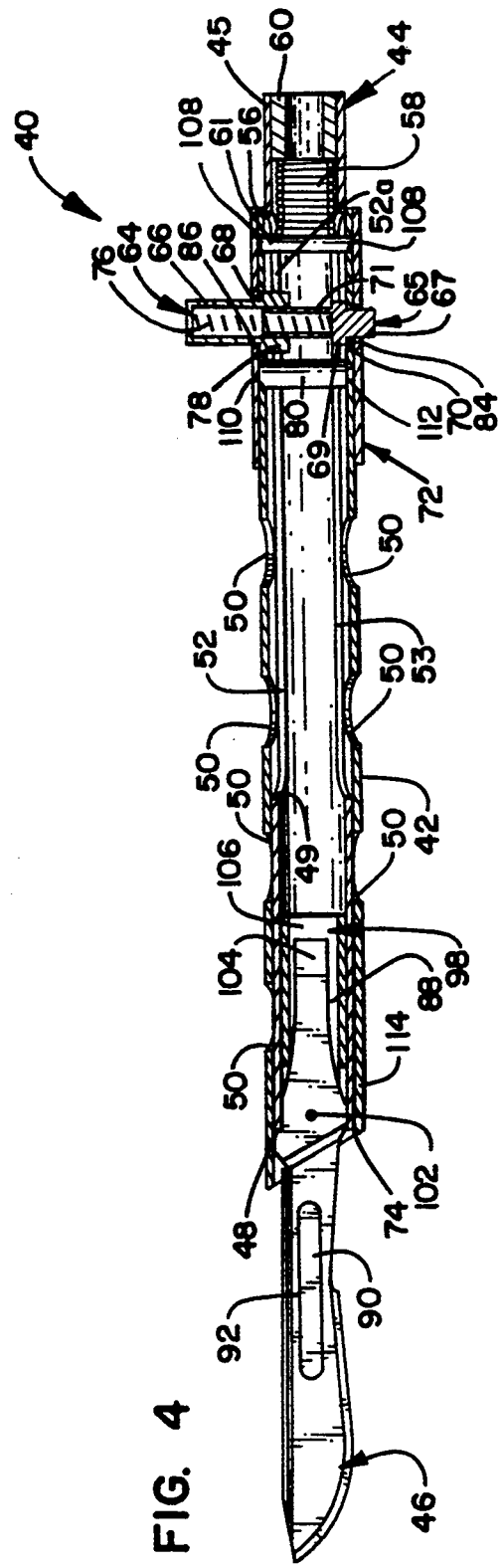

RETRACTABLE SURGICAL KNIFE

This is a continuation-in-part of Ser. No. 07/986,139, filed Dec. 4, 1992, now U.S. Pat. No. 5,292,329.

FIELD OF THE INVENTION

The present invention relates generally to retractable scalpels and similar devices which have a tool/blade movable between an exposed operative position and a covered nonoperative position. In one embodiment, the invention relates to a protective retractable scalpel in which the blade is extended against the force of a spring to expose a cutting surface, and upon completion of the activity, the cutting surface of the blade is quickly and automatically retracted into a sheath.

BACKGROUND OF THE INVENTION

Scalpels are a class of knives used in the surgical environment for incising, stabbing, shaving, and curetting of human and animal tissue. Conventional scalpels used for this purpose have a stationary blade. The blade is always exposed thereby creating a hazard of inadvertent puncture to an operating team member and to any other person who may come in contact with an instrument. The primary hazard of puncture is the possible transmission of an infectious agent, such as the AIDS virus. It has long been a desire of the medical profession to provide a protective scalpel which completely and absolutely encircles and protects the blade during nonuse.

In some emergency situations, a surgeon must work quickly and hand instruments back and forth to assistants. It is dangerous sometimes because the sharp scalpels can accidentally cut or jab the personnel's hands during the operation. Certain fatal infections can be transferred to individuals through small cuts.

Presently existing protective scalpels have removable guards to prevent contact with the blade during nonuse. However, with the rapidity in which surgery is conducted, this imposes a degree of inconvenience which would be burdensome. Other conventional protective scalpels include examples in which a blade sheath pivots or extends and retracts upon a given force applied to a handle of the scalpel. These scalpels do not provide absolute security of the blade such as the present invention where the blade is completely encased in a sheath.

Prior art tool retraction/latch mechanisms have the disadvantage of exposed screws, springs, fasteners, gears, links, and the like which, upon certain conditions, could loosen and fall into a wound or cavity.

Another disadvantage of many protective scalpels is the encroachment of a portion of the scalpel blade. This interfaces with normal use of the scalpel, as entire length of the blade is typically used.

Examples of known prior art are:
U.S. Pat. No. 3,657,812 which discloses a retractable tool holder;
U.S. Pat. No. 5,071,426 which discloses a surgical scalpel with a retractable blade guard;
U.S. Pat. No. 5,116,351 which discloses a safety scalpel having a blade protecting sheath;
U.S. Pat. No. 5,139,507 which discloses a surgical scalpel with a retractable blade guard; and
U.S. Pat. No. 5,141,517 which discloses a retractable instrument automatically actuating the instrument to extend forward from a protective sheath.

The present invention solves many of the problems associated with prior art scalpels and latch mechanisms.

SUMMARY OF THE INVENTION

The present invention provides a tool holder in which a tool retracts into a chassis of the tool holder when not in use such that the tool is shielded.

In one embodiment, it is specifically intended that this tool be a scalpel which functions much like a typical retractable ball point pen with its simple actuation and detent type of release.

One advantage of one embodiment of the present invention is to provide a scalpel having a retractable blade which is relatively inexpensive to produce.

One advantage of the present invention is to provide a scalpel that is free of encumbrance long the entire length of the blade in its extended operative position.

In one embodiment of the present invention, there is provided a scalpel, in either an extended or a retracted position, which has no element or part, such as a pin, screw, fastener, link, or spring, that could become dislodged and be lost in a patient's tissues or body cavity.

In one embodiment of the present invention, the retractable scalpel comprises a tubular sheath member and a tubular blade support member which are secured together by a locking collar.

In one embodiment, the blade support member is slidably mounted and partially disposed in the sheath member. A cutting blade, connectible to one end of the blade support member, is shielded in the sheath member when the scalpel is not in use. The blade is extended from the sheath member and exposed when the scalpel is in its operative position.

Still in one embodiment, when the scalpel is in its operative position, the blade support member is forced forward against the strain of a spring and is locked by a latch mechanism. The blade support member is automatically released by deactuating the latch mechanism when the scalpel is not in use. Accordingly, when the blade support member is forced forward, the cutting blade extends from the sheath member. When the blade support member is released backward, the cutting blade retracts into the sheath member.

Further in one embodiment, a first spring is disposed between a back end of the blade support member and proximate the back end of the sheath member. The spring is compressed in the operative position.

In one embodiment, the blade support member comprises a pair of transversely elongated and longitudinally extended slots wherein one of the slots is disposed at a top side and another slot is disposed at a bottom side of the blade support member. When the scalpel is made into its operating position, the latch mechanism is longitudinally slid along the slots, and is received in an enlarged slot portion disposed proximate a back end of the top side slot.

Still in this embodiment, the latch mechanism includes an upper section, an enlarged section integrated with the upper section, and a lower section. A second spring is compressed under the upper section when the scalpel is not in use. The enlarged section is received into the enlarged slot portion by sliding and pushing the blade support member toward a front end of the blade support member. Upon the receipt of the latch mechanism enlarged section into the enlarged slot portion, the first spring is compressed and the already compressed second spring extends so as to force the enlarged section into the enlarged slot portion so as to lock the blade support member in place.

Still in this embodiment, the latch mechanism is deactuated by transversely compressing the second spring to separate the enlarged section from the enlarged slot portion. The first spring extends backward so as to retract the blade into the sheath member wherein the scalpel is not in use. The latch mechanism serves an additional function in that it prevents the scalpel from rolling more than 180° on a surface.

Furthermore, in one embodiment, a limiting pin and a stop pin are disposed on each side of the latch mechanism which are used to limit the blade extending movement of the blade support member and to stop the blade retracting movement of the blade support member, respectively.

In one embodiment, the blade is removably and securely attached into the blade support member by a blade receiving portion and a fitting member.

In one embodiment, the scalpel is made of stainless steel or any disposable plastic material.

Yet in one embodiment, a plurality of holes are disposed on top and bottom sides of the sheath member so that it reduces the weight of the scalpel, as well as easily washes away blood products from the blade during non-use.

Further in one embodiment, the front end of the sheath member is beveled.

Yet in one embodiment, an external surface of the sheath member is knurled so that the operator can easily control the scalpel during the operation.

In another embodiment, a latch mechanism comprises a tubular member having two aligned longitudinal slots, a key member partially disposed in the tubular member, and a rod. The rod engages with the tubular member and the key member when the scalpel is in use by pushing the blade support member toward the latch mechanism and disengages from the tubular member and the key member when the scalpel is not in use by transversely pushing the tubular member.

Still in another embodiment, a pin connects two opposite walls of the tubular member beside the two slots. An axis of the pin is perpendicular to a longitudinal axis of the tubular member and is perpendicular to a longitudinal axis of the sheath member. A second spring is disposed in the tubular member between a top end of the tubular member and the pin. When the scalpel is in use, the rod is engaged between the pin and the key member by compressing the first spring, and the second spring is further compressed by the top end of the tubular member. After the pin drops into a notch of the rod, the second spring is released by the top end of the tubular member, and the scalpel is locked in an operative position. When the scalpel is not in use, the second spring is compressed by pushing the tubular member downward, the pin is disengaged from the notch of the rod, and the rod is retracted from the tubular member and the key member by an expanding force of the first spring.

Yet in another embodiment, the key member includes a prong portion having top and bottom prongs. The top prong is transversely disposed in the slots between the pin and a bottom end of the second spring, thus the second spring is compressed between the top prong and the top end of the tubular member. The bottom prong is transversely disposed in the slots between the pin and a bottom end of the tubular member. The top and bottom prongs relatively reciprocate in the slots of the tubular member.

Still in another embodiment, the key member includes an arm portion having top and bottom arms being integral with the top and bottom prongs respectively by a connecting portion. The connecting portion has a central hole whereby the rod passes through while engaged. The arm portion and the connecting portion are disposed outside of the slots, and the first spring is disposed between the back end of the tool support member and a back end of the connecting portion. When the scalpel is in use, the first spring is compressed between the back end of the blade support member and the connecting portion, and the rod passes through the space between the top and bottom arms and the central hole of the connecting portion until the rod is engaged with the pin of the tubular member.

Further in another embodiment, the rod has a tapered front portion. The notch is disposed beside the tapered front portion. When the rod is pushed toward the key member, the tapered front portion passes through the central hole and pushes the pin downward by compressing the second spring by the top end of the tubular member, and the movement of the rod is stopped by dropping the pin into the notch. When the tubular member is pushed downward to disengage the pin from the notch, the rod is retracted from the tubular member and the key member by an expanding force of the first spring.

Still in another embodiment, the tapered front portion has a tip and a ramp surface engaging with the pin.

Still in another embodiment, the central hole is aligned with the space between the pin and the top prong when the tapered front portion of the rod passes through the space.

Further in another embodiment, the top and bottom prongs relatively reciprocate in the aligned longitudinal slots, and the relatively reciprocating movement of the prongs is limited by two ends of the slots.

Still in another embodiment, the latch mechanism includes fewer working parts. This provides simpler manufacture as well as making a disposable unit possible with existing technology.

Yet in another embodiment, the latch mechanism substantially eliminates friction forces. The elimination of friction allows safer operation as well as the correct feel of an instrument.

Still in another embodiment, the tool holder includes fewer working parts. This results in a clearer appearance of the tool.

In the second embodiment, the two transverse drill holes of the first embodiment around the top and bottom openings of the sheath member are completely eliminated. In addition, the limiting pin, the stop pin, and the locking collar are eliminated in the second embodiment.

BRIEF DESCRIPTION OF THE DRAWINGS

In the drawing in which like reference numerals and letters generally indicate corresponding parts throughout the several views, FIG. 1 is a perspective view of an embodiment of a retractable scalpel in accordance with the principles of the present invention when the scalpel is in an inoperative retracted position.

FIG. 2 is a perspective view of the scalpel shown in FIG. 1 when the scalpel is in an operative extended position.

FIG. 3 is a longitudinal cross-sectional view of the scalpel shown in FIG. 1 when the scalpel is in an inoperative position.

FIG. 4 is a longitudinal cross-sectional view of the scalpel shown in FIG. 2 when the scalpel is in an operative position.

DETAILED DESCRIPTION OF THE PREFERRED EMBODIMENT

Figure 5:
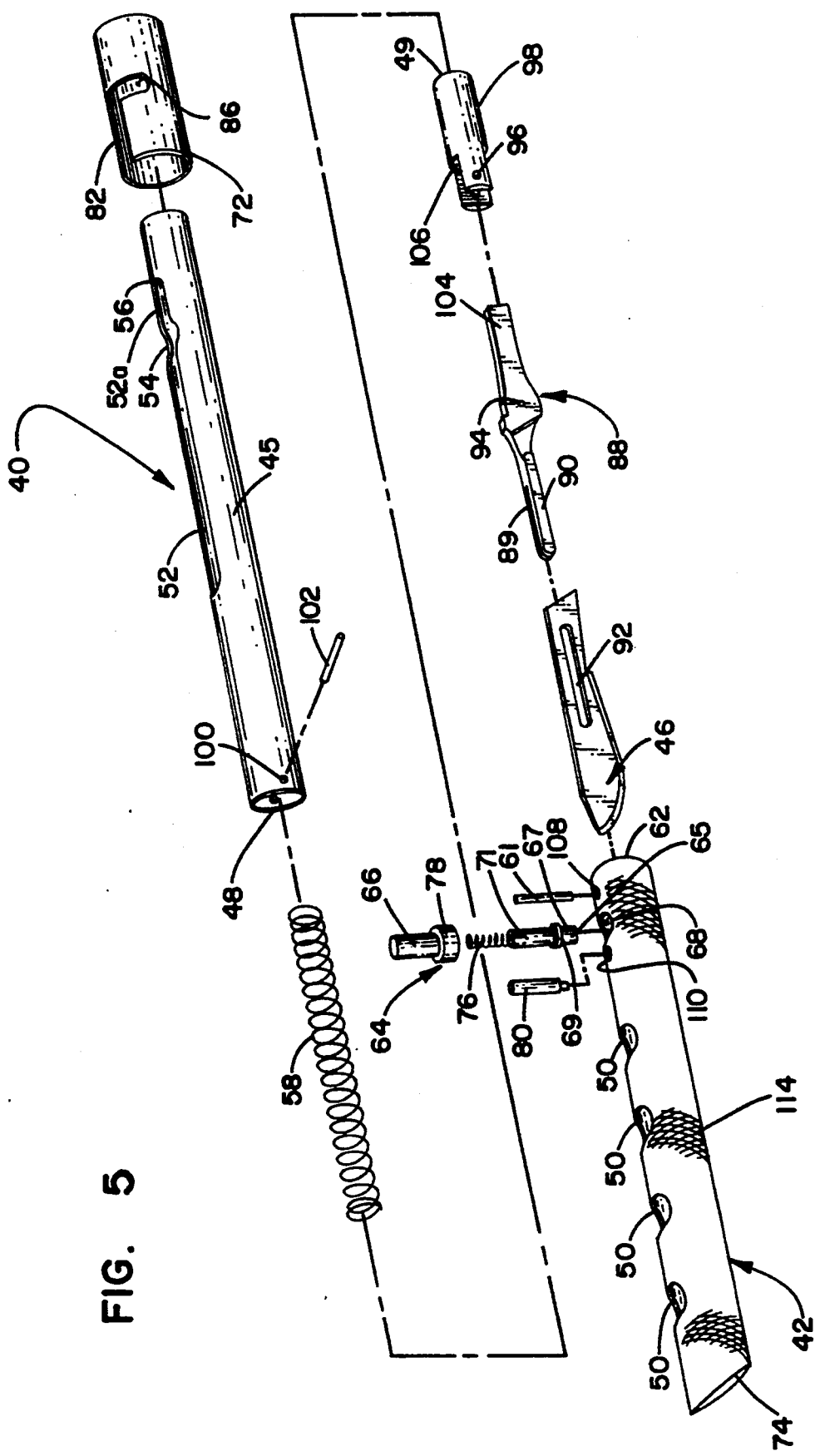
FIG. 5 is an exploded assembly view of the scalpel shown in FIG. 1.

Referring to the Figures, there is shown in FIGS. 1–5 a first embodiment of a retractable scalpel, designated 40, generally in accordance with the principles of the present invention.

The scalpel 40 broadly comprises a tubular barrel or sheath member 42 and a blade support assembly 44 including an inner tubular blade support member 45 which is received telescopically within the sheath member 42. A surgical blade 46, which is mounted on a front end 48 of the blade support assembly 44, is shielded in the sheath member 42. A plurality of holes 50 are disposed on a top side and a bottom side (not shown) of the sheath member 42. The surgical blade 46 is in communication with outside through the holes 50. Accordingly, the holes reduce the weight of the scalpel 40 as well as facillitatively washing away blood products from the blade 46.

The blade support member 45 includes a pair of longitudinally extended, diametrically opposed slots 52,53 wherein the slot 52 is disposed at a top side of the blade support member 45 and the slot 53 is disposed at a bottom side (shown in FIGS. 3, 4) of the blade support member 45. An enlarged slot portion 54 is disposed proximate a back end 56 of the top side slot 52, a portion of the slot 52, shown as a slot portion 52a in FIGS. 3 and 4, extending beyond the enlarged slot portion 54. The slot 53 also extends beyond the enlarged slot portion 54. The enlarged slot portion 54 is able to receive a larger diameter member than the other portion of the top side slot 52. Further, upon receipt of the larger diameter member, which has the diameter larger than the top side slot 52 but smaller than the enlarged slot portion 54, into the enlarged slot portion 54, the member is longitudinally locked relative to the sheath member 42 and the blade support member 45.

A spring 58, which is received between a diameter reducing end cap 60 (see FIG. 3) of the blade support member 45 and a limiting pin 61 at the back end 62 of the sheath member 42, is visible from outside through the slots 52, 53. The spring 58 is compressed or released between the limiting pin 61 and the end cap 60 when the blade support assembly 44 is slidably moved relative to the sheath member 42.

A latch mechanism 64 is disposed proximate the back end 62 of the sheath member 42. The latch mechanism 64 includes a push button section 66, a spring 76 and a bottom section 65 which comprises a bottom pin section 67, a flange section 69 and a hollow section 71. The push button section 66 transversely projects from the top side slot 52 and a top opening 68 of the sheath member 42, while the bottom pin section 67 projects from the bottom side slot 53 and a bottom opening 70 in the sheath member 42 which is diametrically opposite to the top opening 68 (shown in FIG. 3). The openings 68,70 are in transverse alignment with the slots 52,53 wherein the diameter of the top opening 68 is larger than the top side slot 52 and the diameter of the bottom opening 70 is smaller than the slots 52,53.

A locking collar 72 receives the latch mechanism 64, and locks the latch mechanism 64, the sheath member 42 and the blade support assembly 44 together. The structure of the locking collar 72 will be discussed later.

Now referring to FIG. 2, the blade 46 is shown extending from the sheath member 42 in the operative position. The blade support assembly 44 is pushed toward a front end 74 of the sheath member 42 and the spring 58 is compressed accordingly. The front end 74 of the sheath member 42 is beveled. Thus, the whole portion of the blade 46 which contacts a cutting piece (not shown) is wholly exposed so that the surgeon can have a larger view of the cutting piece.

FIGS. 3 and 4 show longitudinal cross-sectional views of FIGS. 1 and 2 respectively, wherein the blade 46 is shielded under the sheath member 42 in FIG. 3 when the scalpel is in the retracted, inoperative position, while the blade 46 is projected from the sheath member 42 in FIG. 4 when the scalpel 40 is in the extended, operative position.

In FIG. 3 the spring 76 is compressedly disposed under the push button section 66 and received in the hollow section 71 of the latch mechanism 46. An enlarged section 78 of the push button section 66, has a larger diameter than the top side slot 52 but smaller than the diameter of the enlarged slot portion 54. Thus, the enlarged section 78 is disposed underneath the top side slot 52 as well as the top opening 68 of the sheath member 42. Accordingly, the spring 76 is kept compressed between the push button section 66 and the bottom section 65 when the scalpel 40 is not in use. As mentioned above, the push button section 66 projects through the top side slot 52 and the top opening 68 of the sheath member 42, while the bottom pin section 67 projects from the bottom side slot 53 and the bottom opening 70 of the sheath member 42.

Now referring to FIG. 4, there is shown a cross-sectional view of the scalpel 40 having the blade extended from the sheath member 42. The blade support assembly 44 is slidably moved toward the front end 74 of the sheath member 42 during which the enlarged section 78 is able to align with the enlarged slot portion 54. When the enlarged section 78 aligns with the enlarged slot portion 54, the enlarged section 78 is automatically received into the enlarged slot portion 54 of the blade support member 45 as well as the top opening 68 as a result of the spring 76 extending. Thereupon, the latch mechanism 64 stops the longitudinal movement between the sheath member 42 and the blade support assembly 44.

The latch mechanism 64 is disposed between the limiting pin 61 and a stop pin 80. The stop pin 80 is aligned with the slots 52,53. The stop pin 80 engages a front end 49 of the slots 52, 53. Thus, the stop pin 80 reduces the possibility of damages of the latch mechanism 64. Upon pushing the push button section 66, the enlarged section 78 is accordingly pushed away from the enlarged slot portion 54 so as to allow the longitudinal movement between the sheath member 42 and the blade support assembly 44. Therefore, the blade support assembly 44 is automatically released backward so as to retract the blade into the sheath member 42.

Now referring to FIG. 5, an exploded view of scalpel 40 is shown. The locking collar 72 includes a L-shape slot 82 on a top side of the locking collar 72, and an opening 84 (shown in FIGS. 3, 4) on a bottom side of the locking collar 72. The push button section 66 is received in a slot terminal point 86 which is disposed at one end of the L-shape slot 82. The bottom pin section 67 projects outside through the bottom opening 84. The diameter of the opening 84 is smaller than that of the slot terminal point 86 so that the opening 84 receives a smaller size of the bottom pin section 67, while the slot terminal point 86 receives a larger size of the push button section 66. Consequently, the L-shape slot 82 secures the sheath member 42, the blade support assembly 44 and the latch mechanism 64 together. Further, the slot terminal point 86 is smaller than the diameter of the enlarged section 78 of the latch mechanism 64. Thus, the locking collar 72 retains the latch mechanism 64 in place on the scalpel 40.

Now referring to the blade 46 and its mounting mechanism. A blade receiving portion 88, having a needle-like head 89, includes a longitudinal projection 90 which is received into a corresponding slot 92 on the blade 46. A through hole 94 which is disposed on the blade receiving portion 88 aligns with a corresponding through hole 96 on a fitting portion 98 and further aligns with a corresponding through hole 100 on the blade support member 45. A pin 102, having a length the same as the diameter of the blade support member 45, passes through the through holes 94,96 and 100 so as to secure the blade 46 onto the blade support member 45. The blade receiving portion 88 can be replaced by removing the pin 102. A back portion 104 of the blade receiving portion 88 is received in a bore 106 of the fitting portion 98. The blade receiving portion 88 and the fitting portion 98 are standard and universal which are able to receive most regular scalpel blades. It will be appreciated that various blade mounting detach mechanisms might be used.

The limiting pin 61, having a length the same as the diameter of the sheath member 42, passes through a pair of transversely opposite openings 108 in the sheath member 42 and extends into the slot portion 52a and the slot 53. The stop pin 80, having a length the same as the diameter of the sheath member 42, passes through a top opening 110 and a transversely opposite bottom opening 112 in the sheath member 42. The stop pin 80 has a top portion larger than a bottom portion which are respectively received in the larger top opening 110 and the smaller bottom opening 112.

The scalpel 40 is made of stainless steal in the preferred embodiment. Alternatively, the scalpel 40 can be made of any kind of metal or plastic materials.

Further, an external surface 114 of the sheath member 42 is knurled so that the surgeon can easily grab or control the scalpel 40 during the operation.

When the scalpel 40 is in use, the blade support assembly 44 is pushed forward. The blade 46 is exposed outside of the sheath member 42 accordingly. The scalpel 40 is locked into an operative position when the enlarged section 78 engages with the enlarged slot portion 54.

When the scalpel 40 is not in use, the push button section 66 is pushed transversely. The blade support assembly 44 is automatically retracted and the blade 46 is accordingly shielded in the sheath member 42.

In assembling the scalpel 40, the longitudinal projection of the blade receiving portion 88 is received in the slot 92 of the blade 46. The blade receiving portion 88 is placed into the bore 106 of the fitting portion 98. The spring 58 is inserted and disposed at the end cap 60. The blade 46, the blade receiving portion 88 and the fitting portion 98 are inserted into the front end 48 of the blade support member 45. The through holes 94, 96 and 100 are aligned to each other and receive the pin 102 therebetween. Thus, the blade assembly 44 is formed.

The blade support assembly 44 is then slidably inserted into the sheath member 42 until the slots 52, 53 align with the openings 68, 70, respectively. The pins 61, 80 are inserted into the openings 108 and 110,112, respectively. The bottom section 65, the spring 76 and the push button section 66 are inserted in the slots 52,53 and the enlarged slot portion 54 from the top opening 68 to the bottom opening 70. The bottom pin section 67 is received in the bottom opening 70 while the flange section 69 stops the further insertion of the bottom pin section 67. The spring 76 is positioned in the hollow section 71 between the bottom pin section 67 and the push button section 66. At this moment, the enlarged section 78 is disposed outside of the top side slot 52. The blade support assembly 44 is pushed to allow the enlarged section 78 aligning with the enlarged slot portion 54 so that the enlarged section 78 is able to move underneath the top side slot 52. The bottom pin section 67 is pushed into the bottom side slot 53 to allow the locking collar 72 to slide over the latch mechanism 64. The locking collar 72 is slid over the back end of 62 the sheath member 42. The locking collar 72 is moved along the L-shaped slot 82 to the position where a clockwise rotation of the locking collar 72 is allowed. Then the locking collar 72 is rotated in a clockwise manner to allow the latch mechanism 64 slide into the slot terminal point 86. The push button section 66 is received in the slot terminal point 86, while the bottom pin section 67 projects through the bottom side slot 53, the bottom opening 70 of the sheath member 42 and the bottom opening 84 of the locking collar 72. Upon this step, the scalpel 40 is assembled.

The scalpel 40 can be disassembled following the reverse procedures of assembling the scalpel 40.

The blade 46 can be replaced by any type of standard scalpel blade. In replacing the blade 46, the blade 46 is simply removed from the longitudinal projection 90 of the blade receiving portion 88.

Figure 6:
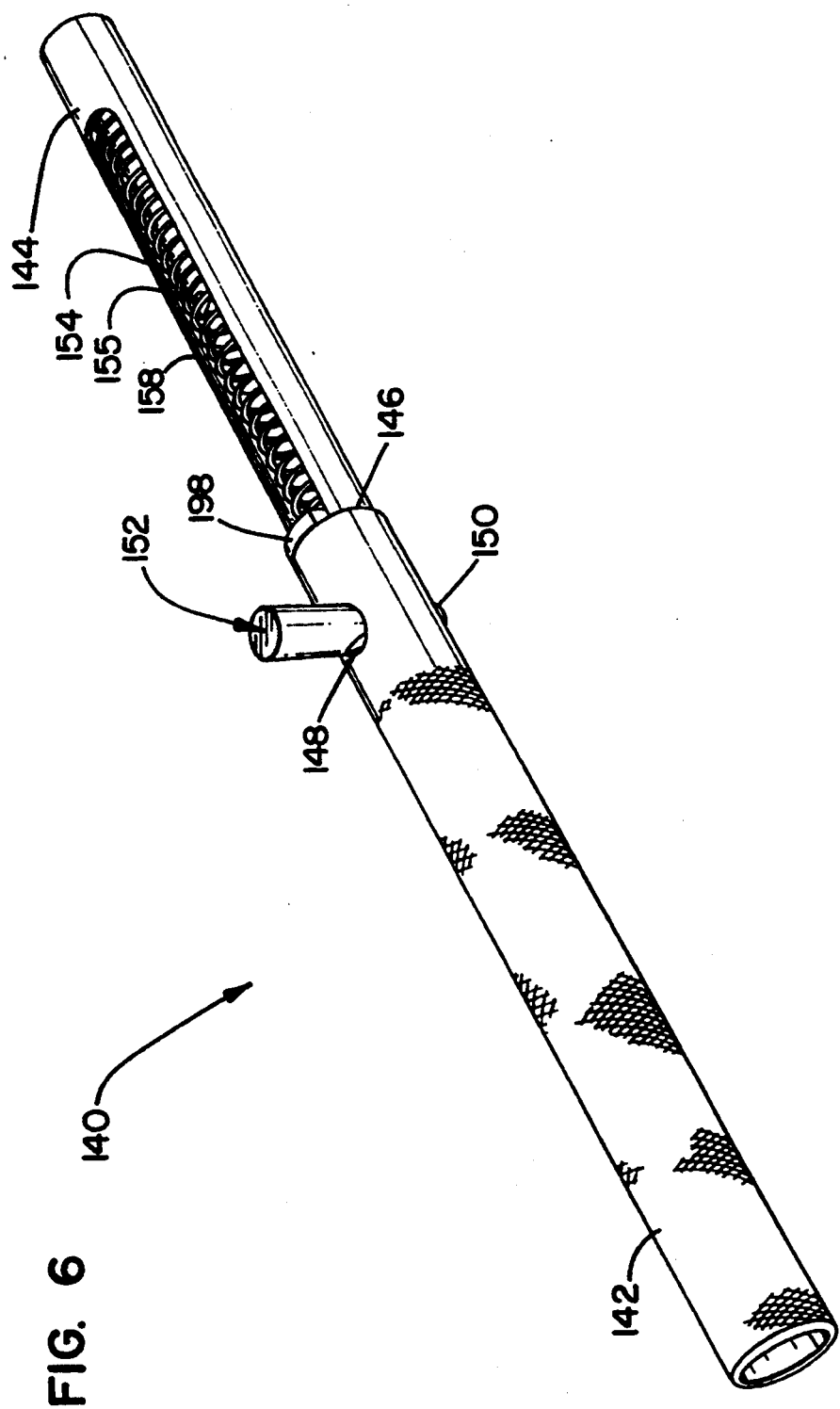
FIG. 6 is a perspective view of a second embodiment of a retractable scalpel in accordance with the principles of the present invention when the scalpel is in an inoperative retracted position.

Referring to FIGS. 6–13, there is shown a second embodiment of a retraction scalpel, designated by the reference numeral 140, generally in accordance with the principles of the present invention. In FIG. 6, the scalpel 140 includes a sheath member 142 and a blade support member 144. The blade support member 144 is telescopically partially received in the sheath member 142 from a back end 146 of the sheath member 142. The sheath member 142 has two aligned transverse holes 148,150 proximate at the back end 146. A latch mechanism 15.2 is transversely partially disposed between the holes 148,150 of the sheath member 142. A first spring 154 is disposed inside the blade support member 144. A rod 155 is telescopically disposed in the spring 154. When the scalpel 140 is not in use as shown in FIG. 6, a blade 156 (see FIG. 8) which is mounted on the front of the blade support member 144 is retracted into the sheath member 142. The spring 154 is released in the blade support member 144. It is preferred that the same mounting means as disclosed in the first embodiment is used to mount the blade 156 onto the blade support member 144. It is appreciated that any other types of mounting means can be used in the second embodiment.

Figure 8:
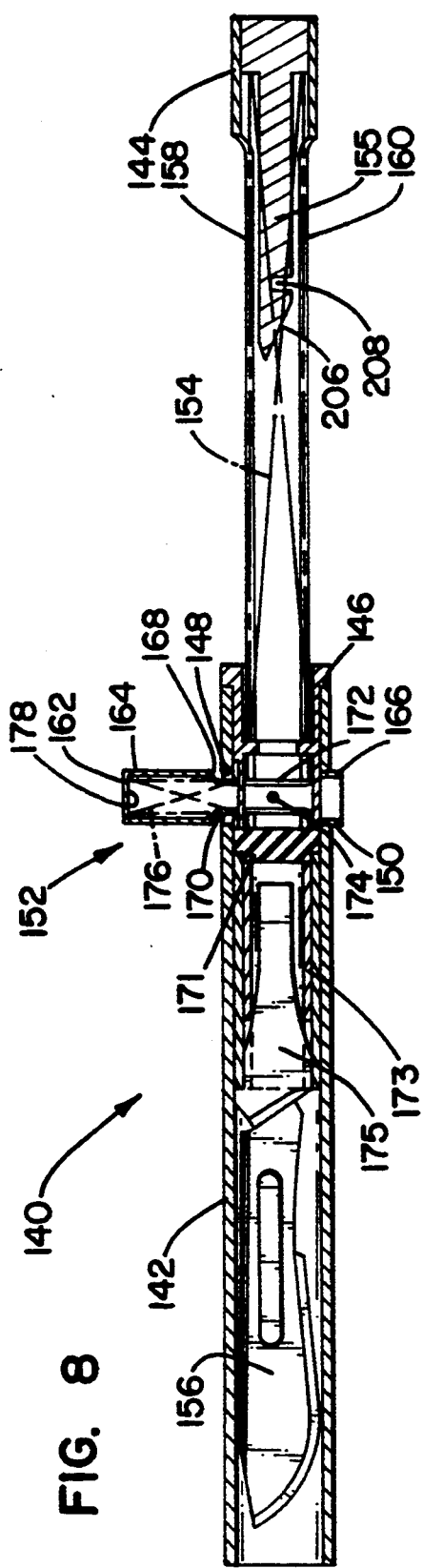
FIG. 8 is a longitudinal cross-sectional view of the second embodiment of the scalpel when the scalpel is in an inoperative position.

The blade support member 144 has top and bottom longitudinally aligned slots 158,160. The bottom slot 160 is shown in FIG. 8. The rod 155 which is displayed through the top and bottom slots 158,160 is integral to the back end of the blade support member 144. The latch mechanism 152 relatively reciprocates in the longitudinally aligned slots 158,160 between front and back ends of the slots 158,160.

Figure 7:
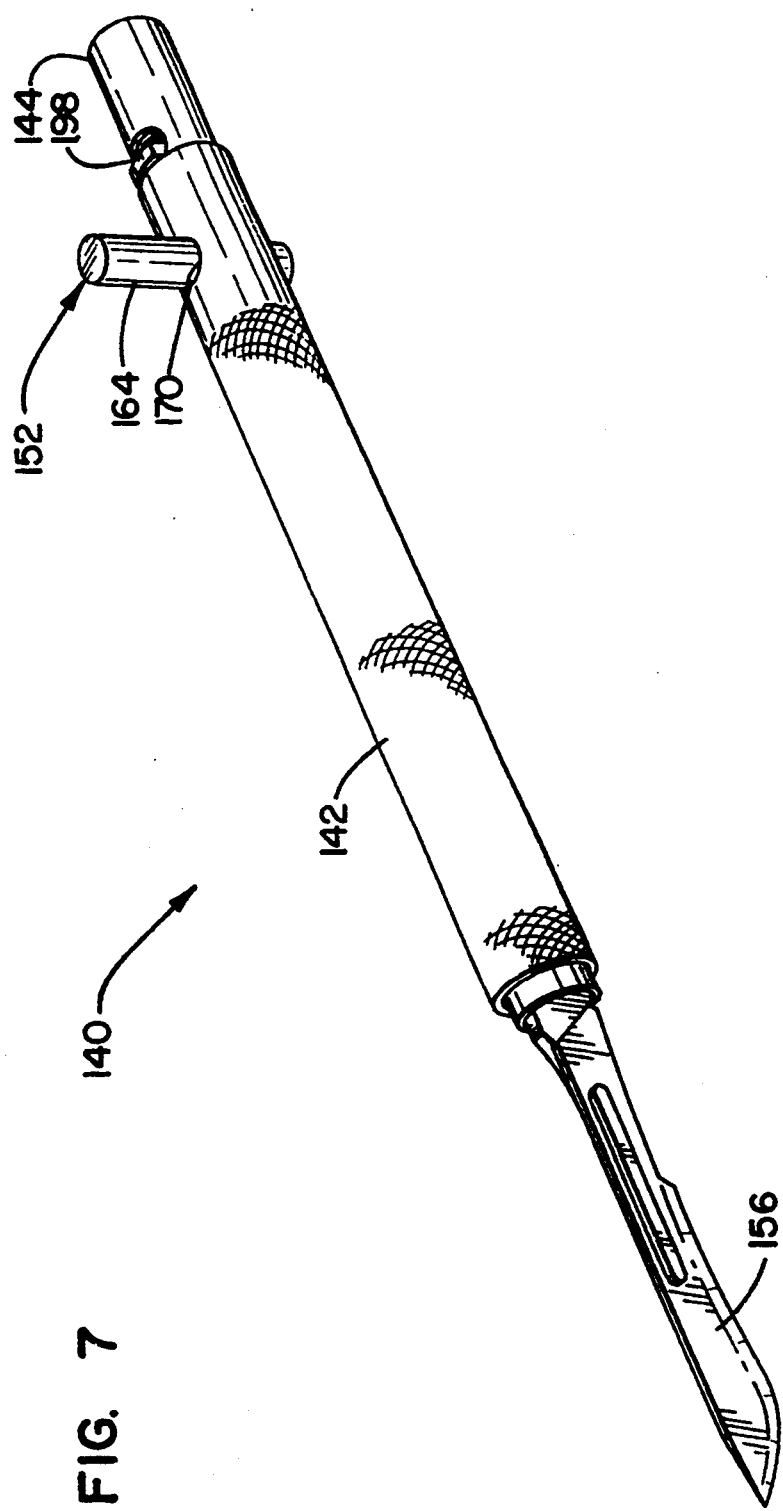
FIG. 7 is a perspective view of the second embodiment of the scalpel when the scalpel is in an operative extended position.

In FIG. 7, the scalpel 140 is in an operative position. The blade 156 is extended from the sheath member 142. The blade support member 144 is pushed toward the latch mechanism 152, whereby the spring 154 is compressed. The latch mechanism 152 locks the scalpel 140 in an operative position.

Figure 9:
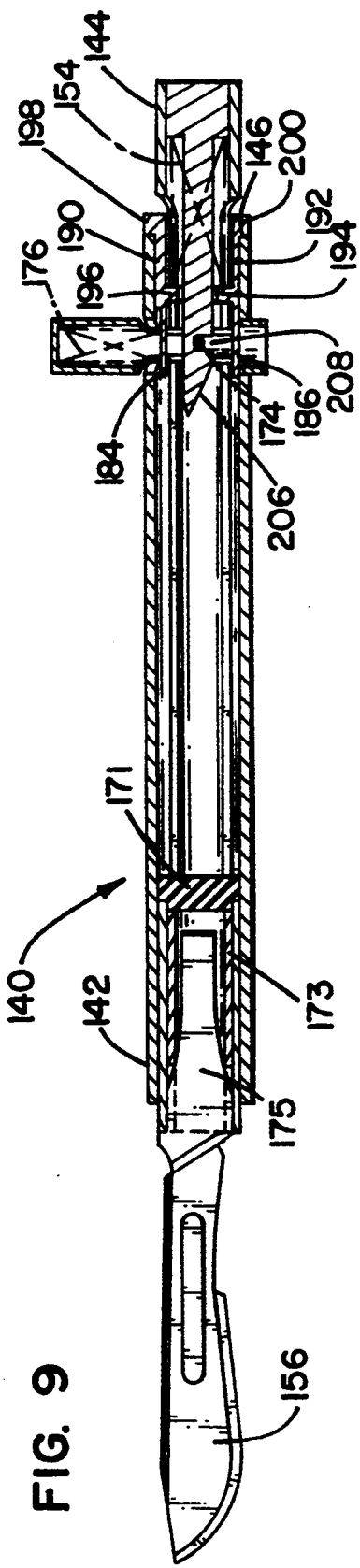
FIG. 9 is a longitudinal cross-sectional view of the second embodiment of the scalpel when the scalpel is in an operative position.

FIGS. 8 and 9 show longitudinal cross-sectional views of the scalpel 140 being in the inoperative position and the operative position, respectively.

In FIG. 8, the latch mechanism 152 includes a tubular member 162 which has a head portion 164 extending out of the hole 148, a foot portion 166 extending out of the hole 150, and a middle portion 168 being substantially disposed in the sheath member 142. The middle portion 168 has two slots 170,172 and two walls beside the slots 170,172. The length of the slots 170,172 is larger than the outer diameter of the blade support member 144 so that the blade support member 144 is able to pass through the latch mechanism 152 to expose the blade 156 from the sheath member 142.

The tubular member 162 further includes a pin 174 which is horizontally disposed between the two walls beside the slots 170,172. The axis of the pin 174 is perpendicular to the longitudinal axis of the tubular member 162 and is perpendicular to the longitudinal axis of the scalpel 140 so that the pin 174 becomes an obstacle for the rod 155 to pass through the tubular member 162.

A second spring 176 is received in the tubular member 162. The top end of the spring 176 is attached to a top closed end 178 of the tubular member 162. The bottom end of the spring is disposed above the pin 174.

Figure 10:
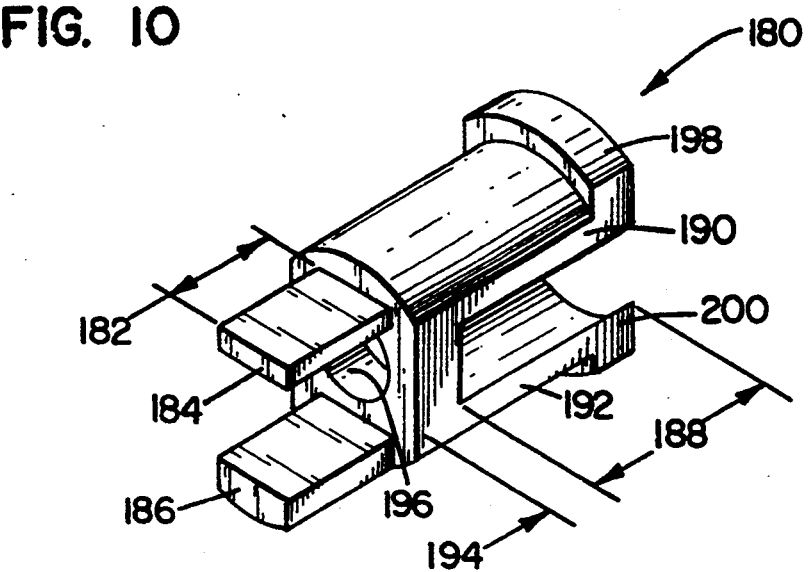
FIG. 10 is an enlarged perspective view of a key member in the second embodiment of the scalpel.
Figure 11:
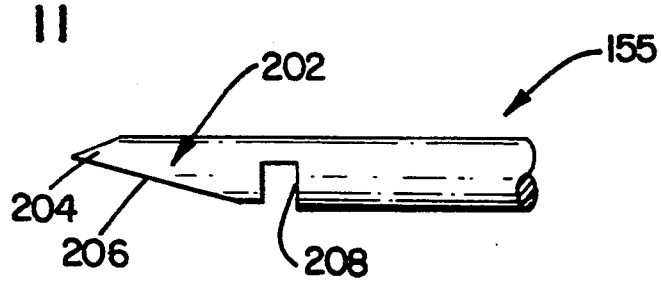
FIG. 11 is an enlarged side view of a rod in the second embodiment of the scalpel.

The latch mechanism 152 further includes a key member 180 (see details in FIG. 10). The key member 180 includes a prong portion 182 having top and bottom prongs 184,186, an arm portion 188 having top and bottom arms 190,192 which are integral with the top and bottom prongs 184,186, respectively, by a connecting portion 194. The connecting portion 194 includes a central hole 196 whereby the rod 155 passes through.

The outer surfaces of the arm portion 188 and the connecting portion 194 are of the same cylindrical contour. The bottom prong 186 has an outer surface aligned to the outer surface of the connecting portion 194 and designed to have the same contour as the outer surface of the connecting portion 194. The top prong 184 has a substantially flat outer surface. The flat outer surface of the top prong 184 is lower than the outer surface of the connecting portion 194. The top and bottom arms 190,192 have rear flanges 198,200, respectively.

Still in FIG. 8, the top prong 184 is vertically disposed in the slots 170,172 between the pin 174 and the bottom end of the second spring 176. The bottom prong 186 is vertically disposed in the slots 170,172 between the pin 174 and the bottom end of the slots 170,172. The second spring 176 is compressed between the top prong 184 and the top end 178 of the tubular member 162, and the bottom prong 186 is engaged with the bottom end of the slots 170,172. The space between the top and bottom prongs 184,186 are smaller than the length of the slots 170,172 so that the prongs 184,186 are relatively movable toward the top end of the slots 170,172 by further compressing the second spring 176. The space between the pin 174 and the highest reaching point of the top prong 184 in the slots 170,172 is large enough for the rod 155 to pass through. The connecting portion 194 and the arm portion 188 are disposed outside of the slots 170,172. The key member 180 is disposed inside of the sheath member 142 except the rear flanges 198,200 are engaged with the back end 146 of the sheath member 142. The external surfaces of the flanges 198,200 have the same contour as the external surface of the sheath member 142 so as to prevent the front end of the connecting portion 194 from abutting the latch mechanism 152. Thus, the tubular member 162 and the key member 180 are detachably engaged with proximate back end 146 of the sheath member 142.

The first spring 154 is disposed between the back end of the blade support member 144 and the back end of the connecting portion 194. When the blade support member 144 is pushed toward the latch mechanism 152, the first spring 154 is compressed and is partially disposed in the space between the top and bottom arms 190,192 (see FIG. 9). Accordingly, the space between the top and bottom arms 190,192 becomes a spring well.

As shown in FIG. 9, the rod 155 is pushed toward the latch mechanism 152. The rod 155 includes a tapered front portion 202 having a tip 204 pointed to the latch mechanism 152. A ramp surface 206 which faces toward the bottom of the latch mechanism 152 is followed the tip 204. The rod 155 further includes a notch 208 rearward of the end of the ramp surface 206. It is preferred that the depth of the notch 208 is about half of the rod diameter. It is appreciated that a different depth can be used.

When the blade support member 144 is pushed toward the latch mechanism 152, the first spring 154 is compressed, and the tapered front portion 202 passes through the space between the top and bottom arms 190,192, the central hole 196, and engages with the pin 174. The central hole 196 functions to maintain proper alignment of the rod 155. In the embodiment shown, a top surface of the central hole 196 acts as a bearing surface for the rod 155. The pin 174 is pushed downward by the ramp surface 206. The second spring 176 is further compressed by the top end 178 of the tubular member 162. After the pin 174 slides over the notch 208, the pin 174 is moved upward by the compressed force of the second spring 176. Accordingly, the pin 174 drops into the notch 208 and engages with the deep end of the notch 208. Thus, the forward movement of the blade support member 144 is stopped, and the blade 156 is extended from the sheath member 142 as shown in FIG. 7 and 9.

To retract the blade 156 into the sheath member 142, the tubular member 162 is pushed down. The pin 174 is disengaged from the notch 208. The space between the pin 174 and the top prong 184 (at the highest reaching point of the slots 170,172 at this moment) is aligned to the central hole 196 and the space between the top and bottom arms 190,192. Since the compressed first spring 154 has the tendency to push the blade support member 144 and the rod 155 backward, the rod 155 moves out of the tubular member 162 and the key member 180 through the slots 170,172, the central hole 196, and the space between the top and bottom arms 190,192. A shock absorber 171 is disposed adjacent a back end of a fitting portion 173, the blade 156 being attached to the fitting portion 173 by a blade receiving portion 175. The shock absorber 171 upon retraction of the blade 156 serves to eliminate shock and damage to the latch mechanism 152. In one embodiment, the shock absorber 171 is made of an elastomeric material.

Since the pin 174 of the latch mechanism 152 is the only obstacle for the rod 155 to overcome, the use of the scalpel 140 is very smooth. The blade support member 144 can be smoothly moved toward the latch mechanism 152 until the engagement between the rod 155 and the pin 174. For the same reason, after the rod 155 disengaged from the pin, the blade support member 144 can be smoothly moved away from the latch mechanism 152. Accordingly, the latch mechanism 152 substantially eliminates the friction forces. The elimination of friction allows safer operation as well as the correct feel of an instrument.

Figure 12:
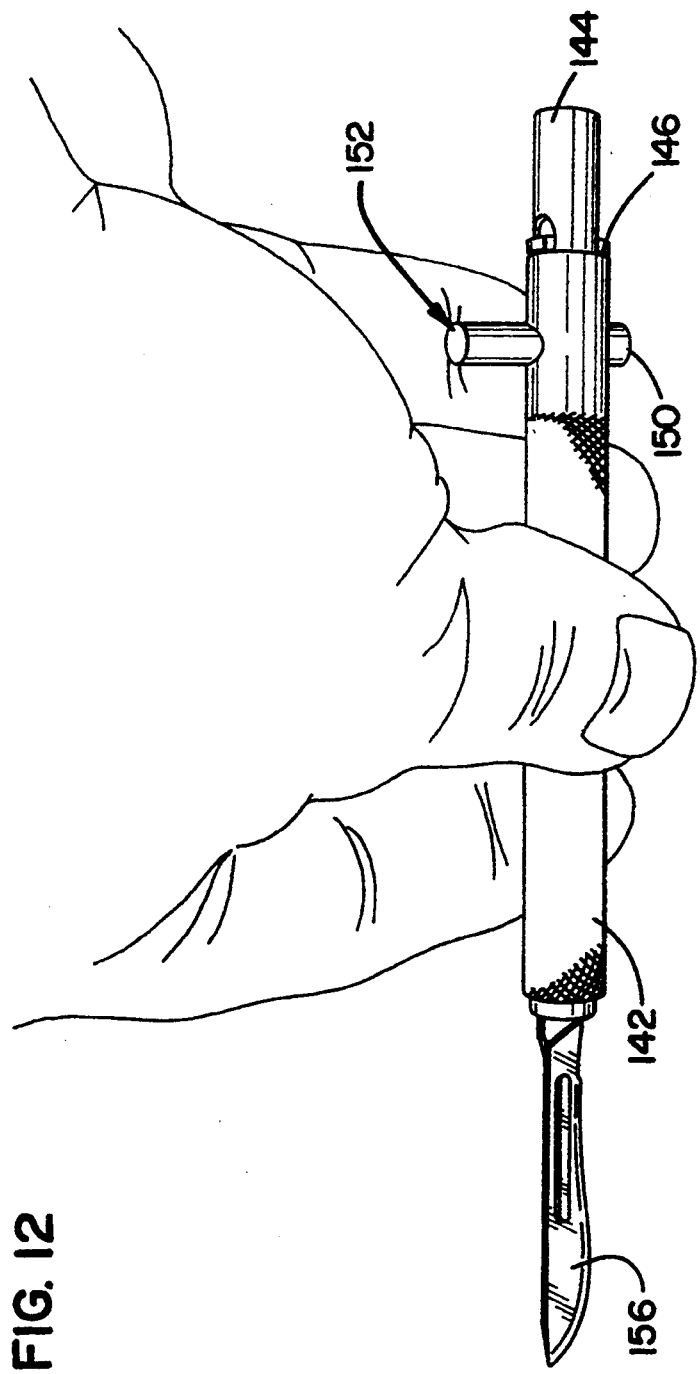
FIG. 12 is a perspective view of the second embodiment of the scalpel being operated by an operator's hand.
Figure 13:
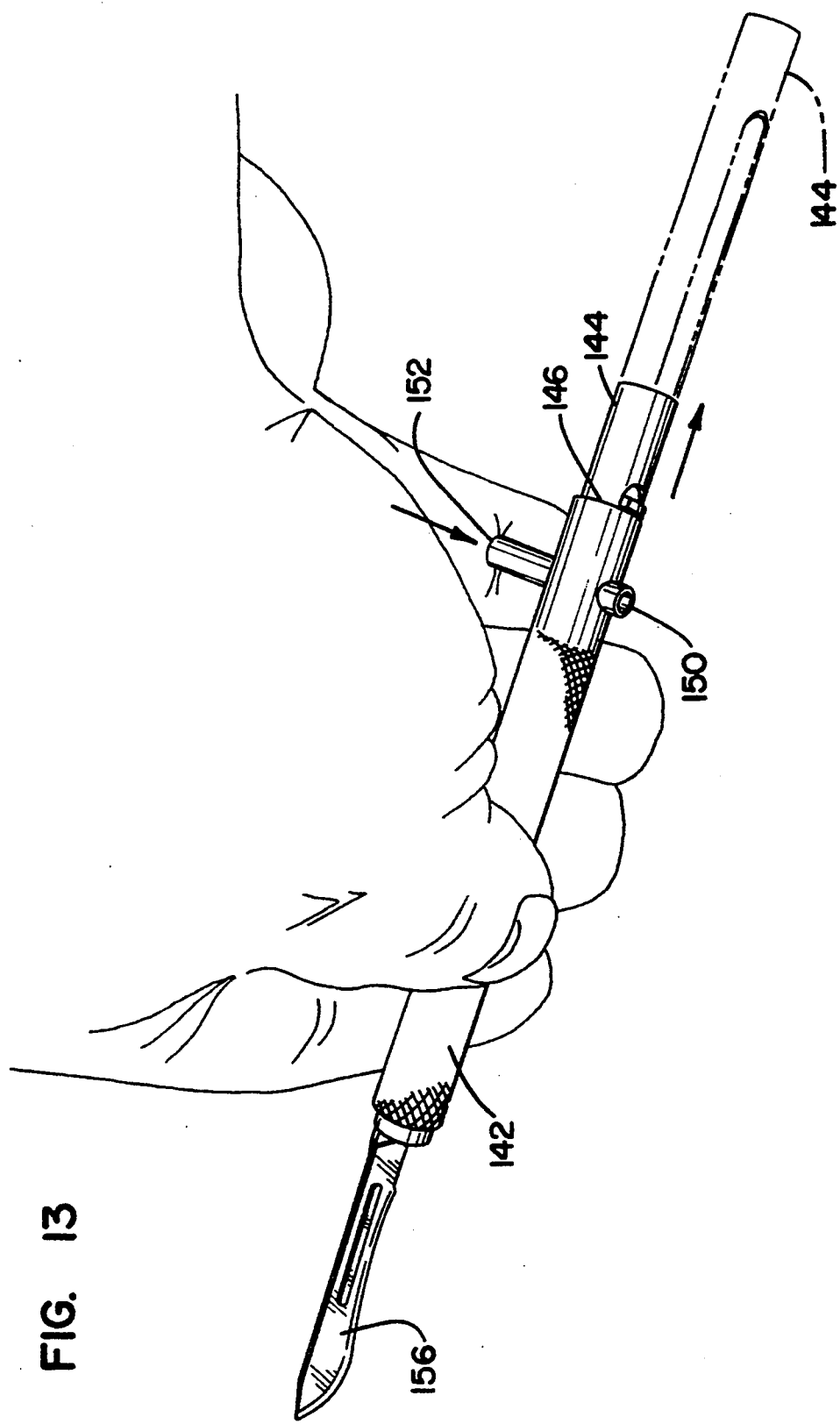
FIG. 13 is a perspective view of the second embodiment of the scalpel being about inoperative by an operator's hand.

FIG. 12 shows the scalpel 140 being used by an operator's right hand. It is appreciated that the scalpel 140 can also be used by an operator's left hand by turning the scalpel 180°. When an operator uses the scalpel 140, the four big thumbs of the operator's hand grab the external surface of the sheath member 142, and the last small thumb leans on the side of the latch mechanism 152. When the operator finishes the use of the scalpel 140, the big thumbs turn the scalpel 140 a certain degree which is enough for the last small thumb to transversely push the tubular member 162 of the latch mechanism 152 downward as shown in FIG. 13. As a result, the blade is to retract into the sheath member 142.

The external surface of the sheath member 142 is knurled so as to allow the operator to easily grab or turn or control the scalpel 140 during an operation. In the second embodiment, there is no hole on the external surface of the sheath member 142 so that the operator's gloves are not caught in the holes.

The scalpel 140 is made of stainless steel. The scalpel 140 except the blade can also be made of plastic materials. It is appreciated that any other types of materials, such as metal, can be used to make the same.

The length of the scalpel 140 is about 5.56 inches (141.22 mm). The length of the sheath member 142 and the length of the blade support member 144 are about 71.93 mm, respectively. The inclining degree of the ramp surface 206 of the rod 155 is about 23°.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A retractable tool holder, comprising:
   a tool support member having front and back ends, the tool support member holding a tool at a front end, including at least one longitudinally extended slot;
   a sheath member having front and back ends, the sheath member telescopically at least partially receiving the tool support member;
   a spring being disposed inside the tool support member proximate the back end of the tool support member;
   a latch mechanism, disposed proximate the back end of the sheath member, relatively reciprocating in a slot of the tool support member, movement of the back end of the tool support member toward the latch mechanism extending the tool out of the sheath member and compressing the spring toward the front end of the tool support member, movement of the back end of the tool support member away from the latch mechanism retracting the tool into the sheath member and expanding the spring toward the back end of the tool support member.

2. A retractable tool holder in accordance with claim 1, wherein the tool is a blade.

3. A retractable tool holder, comprising:
   a sheath member having front and back ends and two transversely aligned holes proximate at said back end;
   a tool support member partially disposed in the sheath member having front and back ends;
   a tool being mounted onto the front end of the tool support member;
   said tool support member being telescopically received in the sheath member for movement between an inoperative position wherein the tool is retracted into the sheath member and an operative position wherein the tool extends from the sheath member;
   said tool support member having at least one transversely elongated and longitudinally extended slot, a first spring being disposed inside of the tool support member, the first spring being compressed upon movement of the tool support member into the sheath member;
   a latch mechanism for locking the tool in said operative position and releasing the tool from said operative position, comprising:
      a tubular member having a top end and a bottom end, the tubular member extending and being partially disposed in said two transversely aligned holes of the sheath member, the tubular member having two aligned longitudinal slots and two opposite walls beside the two aligned longitudinal slots, a pin connecting the two opposite walls, an axis of said pin being perpendicular to a longitudinal axis of said tubular member and being perpendicular to a longitudinal axis of said sheath member, and a second spring being disposed between the top end of the tubular member and the pin, the second spring having top end and a bottom end;

a key member including a prong portion having top and bottom prongs, the top prong being transversely disposed in the two aligned longitudinal slots between the pin and the bottom end of the second spring, the bottom prong being transversely disposed in the two aligned longitudinal slots between the pin and the bottom end of the tubular member, an arm portion having top and bottom arms being integral with the top and bottom prongs respectively by a connecting portion, said connecting portion having a central hole and a back end, the arm portion and the connecting portion being disposed outside of the two aligned longitudinal slots, the first spring being disposed between the back end of the tool support member and the back end of the connecting portion;

a rod integral with the back end of the tool support member being telescopically disposed in the first spring, the rod having a tapered end portion and a notch, the notch being disposed beside the tapered end portion;

the rod being pushed toward the key member and the tubular member when the tool holder is in operation, wherein the tapered end portion passes through the central hole and engages with the pin, upon pushing the pin down by the tapered end portion by compressing the second spring by the top end of the tubular member, and upon the pin dropping into the notch, the forward movement of the rod is stopped, and the first spring is compressed; and the tubular member being pushed downward to disengage the pin from the notch when the tool holder is inoperative, wherein the rod is retracted from the tubular member and the key member by an expanding force of the first spring.

4. A retractable tool holder in accordance with claim 3, wherein the tapered end portion having a tip and a ramp surface engaged with the pin.

5. A retractable tool holder in accordance with claim 3, wherein the central hole is aligned with the space between the pin and the top prong when the tapered end portion of the rod passes through said space.

6. A retractable tool holder in accordance with claim 3, wherein the top and bottom prongs relatively reciprocate in said aligned longitudinal slots of the tubular member, the relatively reciprocating movement of said prongs being limited by two ends of the aligned longitudinal slots of the tubular member.

7. A retractable tool holder in accordance with claim 3, wherein the arm portion has top and bottom rear flanges integral with the top and bottom arms, respectively, the rear flanges having the same outer diameter as an outer diameter of the sheath member so that the rear flanges are engaged with the back end of the sheath member.

8. A retractable tool holder in accordance with claim 3, wherein the longitudinal slot of the tool support member receives the latch mechanism, the latch mechanism is relatively reciprocated along the slot of the tool support member.

9. A retractable tool holder in accordance with claim 3, wherein the tool is a blade.

10. A retractable tool holder in accordance with claim 3, wherein the tool holder is made of stainless steel.

11. A retractable tool holder in accordance with claim 3, wherein the tool holder is made of metal.

12. A retractable scalpel in accordance with claim 3, wherein the tool holder is made of plastic material.

13. A retractable scalpel, comprising:

a sheath member having front and back ends, and two transversely aligned holes proximate at the back end;

a blade support member partially disposed in the sheath member having front and back ends;

a blade being mounted onto the front end of the blade support member;

the blade support member being telescopically received in the sheath member for movement between an inoperative position wherein the blade is retracted into the sheath member and an operative position wherein the blade extends from the sheath member;

said blade support member having at least one transversely elongated and longitudinally extended slot, a first spring being disposed inside of the blade support member, the first spring being compressed upon movement of the blade support member into the sheath member;

a latch mechanism for locking the blade support member in said operative position and releasing the blade support member from said operative position, comprising:

a tubular member having a top end and a bottom end, the tubular member extending and being partially disposed in said two transversely aligned holes of the sheath member, the tubular member having two aligned longitudinal slots and two opposite walls beside the aligned longitudinal slots, a pin connecting the two opposite walls, an axis of said pin being perpendicular to a longitudinal axis of said tubular member and being perpendicular to a longitudinal axis of the sheath member, and a second spring being disposed between the top end of the tubular member and the pin the second spring having a top end and a bottom end;

a key member including a prong portion having top and bottom prongs, the top prong being transversely disposed in the two aligned longitudinal slots between the pin and the bottom end of the second spring, the bottom prong being transversely disposed in the two aligned longitudinal slots between the pin and the bottom end of the tubular member, an arm portion having top and bottom arms being integral with the top and bottom prongs respectively by a connecting portion, said connecting portion having a central hole and a back end, the arm portion and the connecting portion being disposed outside of the two aligned longitudinal slots, the first spring being disposed between the back end of the blade support member and the back end of the connecting portion;

a rod integral with the back end of the blade support member being telescopically disposed in the first spring, the rod having a tapered end portion and a notch, the notch being disposed beside the tapered end portion;

the rod being pushed toward the key member and the tubular member when the scalpel is in operation, wherein the tapered end portion passes through the central hole and engages with the pin, upon pushing the pin down by the tapered end portion by compressing the second spring by the top end of the tubular member, and upon the pin dropping into the notch, the forward movement of the rod is stopped, and the first spring is compressed; and the tubular member being pushed downward to disengage the pin from the notch when the scalpel is inoperative, wherein the rod is retracted from the tubular member and the key member by an expanding force of the first spring.

14. A latch mechanism, comprising:

a tubular member having two aligned longitudinal slots and two opposite walls beside the two aligned longitudinal slots, the tubular member further having a top end and a bottom end, a pin connecting the two opposite walls, an axis of said pin being perpendicular to a longitudinal axis of said tubular member, a resilient member having a top end and a bottom end, the resilient member being disposed between the top end of the tubular member and the pin;

a key member including a prong portion having top and bottom prongs, the top prong being transversely disposed between the pin and the bottom end of the resilient member, the bottom prong being transversely disposed between the pin and the bottom end of the tubular member, an arm portion having top and bottom arms being integral with the top and bottom prongs respectively by a connecting portion, said connecting portion having a central hole;

a rod having a tapered end portion and a notch, the notch being disposed beside the tapered end portion;

the rod being inserted through a space between the top and bottom arms when the latch mechanism is actuated, upon passing the tapered end portion through the central hole and pushing the pin down by the tapered end portion by compressing the resilient member by the top end of the tubular member, the forward movement of the rod is stopped by dropping the pin into the notch; and the tubular member being pushed downward to disengage the pin from the notch when the latch mechanism is disactuated, wherein the rod is retracted from the tubular member and the key member.

15. A latch mechanism in accordance with claim 14, wherein the tapered end portion having a tip point and a ramp surface engaging with the pin.

16. A latch mechanism in accordance with claim 14, wherein the central hole is aligned with the space between the pin and the top prong when the tapered end portion of the rod passes through said space.

17. A latch mechanism in accordance with claim 14, wherein the top and bottom prongs relatively reciprocate in said aligned longitudinal slots of the tubular member, the relatively reciprocating movement of said prongs being limited by two ends of said slots of the tubular member.

* * * * *